(12) United States Patent
DiFoggio et al.

(10) Patent No.: US 7,614,302 B2
(45) Date of Patent: Nov. 10, 2009

(54) ACOUSTIC FLUID ANALYSIS METHOD

(75) Inventors: Rocco DiFoggio, Houston, TX (US); Paul A. Bergren, Houston, TX (US); Jun Han, Kingwood, TX (US)

(73) Assignee: Baker Hughes Incorporated, Houston, TX (US)

( * ) Notice: Subject to any disclaimer, the term of this patent is extended or adjusted under 35 U.S.C. 154(b) by 354 days.

(21) Appl. No.: 11/638,893

(22) Filed: Dec. 14, 2006

(65) Prior Publication Data

US 2007/0129901 A1 Jun. 7, 2007

Related U.S. Application Data

(63) Continuation-in-part of application No. 11/194,365, filed on Aug. 1, 2005, now Pat. No. 7,523,640.

(51) Int. Cl.
*G01N 29/04* (2006.01)
*G01N 29/50* (2006.01)

(52) U.S. Cl. ........................................ 73/597; 73/602

(58) Field of Classification Search .................. 73/1.82, 73/1.83, 1.86, 24.06, 32 A, 54.41, 61.49, 73/64.53, 597, 598, 602

See application file for complete search history.

(56) References Cited

U.S. PATENT DOCUMENTS

| | | | |
|---|---|---|---|
| 4,416,152 A | | 11/1983 | Wilson |
| 4,571,693 A | | 2/1986 | Birchak et al. |
| 4,769,793 A | * | 9/1988 | Kniest et al. ................... 367/99 |
| 4,938,066 A | * | 7/1990 | Dorr ............................ 73/597 |
| 5,635,626 A | | 6/1997 | Hammond et al. |
| 6,029,507 A | * | 2/2000 | Faber et al. ................. 73/61.75 |
| 6,032,516 A | * | 3/2000 | Takahashi et al. ........... 73/64.53 |
| 6,199,423 B1 | | 3/2001 | Logue et al. |
| 6,575,043 B1 | | 6/2003 | Huang et al. |
| 6,634,214 B1 | | 10/2003 | Thurston et al. |
| 6,672,163 B2 | | 1/2004 | Han et al. |
| 6,763,698 B2 | * | 7/2004 | Greenwood ................. 73/30.01 |
| 6,817,229 B2 | | 11/2004 | Han et al. |
| 7,024,917 B2 | | 4/2006 | DiFoggio |
| 2001/0010174 A1 | | 8/2001 | Matsiev et al. |
| 2001/0039829 A1 | | 11/2001 | Wenger et al. |
| 2001/0054305 A1 | | 12/2001 | Banda et al. |
| 2002/0035879 A1 | | 3/2002 | Shine et al. |

(Continued)

OTHER PUBLICATIONS

Terra E. Bulloch, The Investigation of Fluid Properties & Seismic Attributes for Reservoir Characterization, Thesis for degree of Masterof Ascience in Geological Engineering, Michigan Technological University, 1999, pp. A1-A6.

(Continued)

*Primary Examiner*—Hezron Williams
*Assistant Examiner*—Rose M Miller
(74) *Attorney, Agent, or Firm*—Bracewell & Giuliani

(57) ABSTRACT

A method of analyzing acoustic data, that includes determining fluid sound speed through connate fluid. The method involves sampling the fluid, sending an acoustic signal into the fluid between a first and a second reflective interface. Data is recorded that represents acoustic signals over time as they are reflecting from the interfaces. A smoothed first derivative with respect to time of the cumulative sum of squares (CSS) of the filtered amplitude data is determined. This first derivative is cross correlated to the time-shifted versions of itself.

23 Claims, 4 Drawing Sheets

U.S. PATENT DOCUMENTS

| | | |
|---|---|---|
| 2002/0100326 A1 | 8/2002 | Stein |
| 2002/0100327 A1 | 8/2002 | Kersey et al. |
| 2002/0112540 A1 | 8/2002 | Zeroug et al. |
| 2002/0117003 A1 | 8/2002 | Banno et al. |
| 2002/0134612 A1 | 9/2002 | Khan |
| 2002/0170341 A1 | 11/2002 | Jakoby et al. |
| 2002/0178787 A1 | 12/2002 | Matsiev et al. |
| 2002/0178805 A1 | 12/2002 | DiFoggio et al. |
| 2002/0184940 A1 | 12/2002 | Storm et al. |
| 2002/0189367 A1 | 12/2002 | Gomm et al. |
| 2002/0194906 A1 | 12/2002 | Goodwin et al. |
| 2003/0029241 A1 | 2/2003 | Mandal |
| 2003/0029242 A1 | 2/2003 | Varalioglu et al. |
| 2003/0051535 A1 | 3/2003 | Coupland et al. |
| 2003/0061868 A1 | 4/2003 | Povey et al. |
| 2003/0065447 A1 | 4/2003 | Bramlett et al. |
| 2003/0101819 A1 | 6/2003 | Mutz et al. |
| 2003/0101820 A1 | 6/2003 | Siong |
| 2003/0136186 A1 | 7/2003 | Gysling |
| 2003/0150257 A1 | 8/2003 | Mutz et al. |
| 2003/0150262 A1 | 8/2003 | Han et al. |
| 2003/0172734 A1 | 9/2003 | Greenwood |
| 2003/0188580 A1 | 10/2003 | Cardelius |
| 2003/0196477 A1 | 10/2003 | Auner et al. |
| 2003/0209066 A1 | 11/2003 | Goodwin |
| 2003/0213304 A1 | 11/2003 | Toda |
| 2003/0216874 A1 | 11/2003 | Henry et al. |
| 2003/0217589 A1 | 11/2003 | Jakoby et al. |
| 2003/0221489 A1 | 12/2003 | Koo |
| 2003/0221490 A1 | 12/2003 | Sauerland |
| 2004/0006409 A1 | 1/2004 | Liljenberg et al. |
| 2004/0007058 A1 | 1/2004 | Rylander et al. |
| 2004/0015303 A1 | 1/2004 | Severson et al. |
| 2004/0016298 A1 | 1/2004 | Scott |
| 2004/0020294 A1 | 2/2004 | Buckin |
| 2004/0035190 A1 | 2/2004 | Sinha |
| 2004/0060344 A1 | 4/2004 | Kauffman et al. |
| 2004/0060345 A1 | 4/2004 | Eggen et al. |
| 2004/0119793 A1 | 6/2004 | Mutz et al. |
| 2004/0139798 A1 | 7/2004 | Haddad et al. |
| 2004/0172197 A1 | 9/2004 | Fehmers et al. |
| 2004/0173017 A1 | 9/2004 | O'Brien |
| 2004/0177692 A1 | 9/2004 | Sadri et al. |
| 2004/0194539 A1 | 10/2004 | Gysling |
| 2004/0216515 A1 | 11/2004 | Yakhno et al. |
| 2004/0226378 A1 | 11/2004 | Oda et al. |
| 2004/0231402 A1 | 11/2004 | Eisenschmid et al. |
| 2004/0236512 A1 | 11/2004 | DiFoggio et al. |
| 2005/0005676 A1 | 1/2005 | Crawley et al. |
| 2005/0015000 A1 | 1/2005 | Djennati et al. |
| 2005/0028579 A1 | 2/2005 | Owen |
| 2005/0034536 A1 | 2/2005 | Kondo |
| 2005/0043890 A1 | 2/2005 | Sanstrom |
| 2005/0043906 A1 | 2/2005 | Funck et al. |
| 2005/0072236 A1 | 4/2005 | Heyman et al. |
| 2005/0103096 A1 | 5/2005 | Jakoby et al. |
| 2005/0103097 A1 | 5/2005 | Faltum et al. |
| 2005/0109087 A1 | 5/2005 | Robb et al. |
| 2005/0149277 A1 | 7/2005 | Bailey et al. |
| 2005/0155416 A1 | 7/2005 | Ouellette et al. |
| 2005/0171710 A1 | 8/2005 | Gysling et al. |
| 2005/0193805 A1 | 9/2005 | Williams et al. |
| 2005/0212869 A1 | 9/2005 | Elison et al. |
| 2005/0223808 A1 | 10/2005 | Myers et al. |
| 2005/0247116 A1 | 11/2005 | Wenger et al. |
| 2005/0252286 A1 | 11/2005 | Ibrahim et al. |
| 2005/0252294 A1 | 11/2005 | Ariav |
| 2005/0252884 A1 | 11/2005 | Lam et al. |
| 2005/0268703 A1 | 12/2005 | Funck et al. |
| 2005/0284210 A1 | 12/2005 | Schmidt et al. |
| 2006/0020404 A1 | 1/2006 | Kishiro et al. |
| 2006/0032295 A1 | 2/2006 | Hazelden et al. |
| 2006/0048583 A1 | 3/2006 | Gysling |
| 2006/0065046 A1 | 3/2006 | Battiston et al. |
| 2006/0101916 A1 | 5/2006 | Griffiths et al. |
| 2006/0156797 A1 | 7/2006 | Mutz et al. |
| 2006/0236758 A1 | 10/2006 | DiFoggio et al. |
| 2006/0243047 A1 | 11/2006 | Terabayashi et al. |
| 2006/0266109 A1 | 11/2006 | DiFoggio |
| 2006/0277979 A1 | 12/2006 | Fitch et al. |
| 2007/0013381 A1 | 1/2007 | Biberger |
| 2007/0022803 A1 | 2/2007 | DiFoggio et al. |
| 2007/0068242 A1 | 3/2007 | DiFoggio |
| 2007/0084286 A1 | 4/2007 | Ajay et al. |
| 2007/0101804 A1 | 5/2007 | Billson |
| 2007/0119232 A1 | 5/2007 | Konno et al. |
| 2007/0125163 A1 | 6/2007 | Dria et al. |
| 2007/0129901 A1 | 6/2007 | DiFoggio et al. |
| 2007/0137286 A1 | 6/2007 | Neyens |
| 2007/0137292 A1 | 6/2007 | Xian et al. |
| 2007/0144240 A1 | 6/2007 | Andle |
| 2007/0151340 A1 | 7/2007 | Hsu et al. |
| 2007/0162239 A1 | 7/2007 | Lang |

OTHER PUBLICATIONS

Abraham Savitzky & Marcel J. E. Golay, Smoothing and Differentiation of Date by Simplified Least Squares Procedures, Analytical Chemistry, Internatioinal Gas Chromatography Symposium, vol. 36, No. 8, Jul. 1964—pp. 1627-1639.

Reservoir characterization Instrument, pamphlet from Baker Hughes, Copyright 2000 Baker Hughes Incorporated.

Sitakanta Mohanty, Effect of Multiphase Fluid Saturation on the Thermal Conductivity of Geologic Media, J. Phys. D. Appl. Phys., 30, No. 24 (Dec. 21, 1997), pp. L80-L84.

International Search Report dated Jul. 25, 2008.

* cited by examiner

ACOUSTIC FLUID ANALYSIS METHOD

RELATED APPLICATIONS

This application is a continuation-in-part of U.S. application Ser. No. 11/194,365 filed Aug. 1, 2005 now U.S. Pat. No. 7,523,640, the full disclosure of which is hereby incorporated by reference herein.

BACKGROUND OF THE INVENTION

1. Field of the Invention

The invention relates to wellbore evaluation operations. More specifically, the present invention relates to an apparatus and method for ascertaining the compressibility of connate fluid within a wellbore and the presence of a gaseous phase in that fluid.

2. Description of Related Art

The sampling of connate fluid contained in subterranean formations provides a method of testing formation zones of possible interest with regard to hydrocarbon bearing potential. This involves recovering a sample of any formation fluids present for later analysis in a laboratory environment while causing a minimum of damage to the tested formations. The formation sample is essentially a point test of the possible productivity of subsurface earth formations. Additionally, a continuous record of the control and sequence of events during the test is made at the surface. From this record, valuable formation pressure and permeability data as well as data determinative of fluid compressibility, density and viscosity can be obtained for formation reservoir analysis.

Generally connate fluid sampling involves disposing a sonde 10 into a wellbore 5 via a wireline 8. Oppositely located on the outer portion of the sonde 10 usually are a sample port 14 and an urging means 12. When the sample port 14 is proximate to a formation of interest 6, the urging means 12 is extended against the inner surface of the wellbore 5 thereby engaging the sample port 14 into the formation 6. The engagement of the sample port 14 pierces the outer diameter of the wellbore 5 and enables fluid communication between the connate fluid in the formation 6 and the sample port 14. After urging the sample port 14 into the formation 6, the connate fluid can be siphoned into the sonde 10 with a pumping means disposed therein.

Downhole multi-tester instruments have been developed with extendable sampling probes that engage the borehole wall and withdraw fluid samples from a formation of interest as well as measure pressure of the fluid within the formation. Traditionally these downhole instruments comprise an internal draw-down piston that is reciprocated hydraulically or electrically for drawing connate fluid from the formation to the instrument.

Generally, the downhole multi-test sampling devices incorporate a fluid circuit for the sampling system which requires the connate fluid extracted from the formation, together with any foreign matter such as fine sand, rocks, mud-cake, etc. encountered by the sampling probe, to be drawn into a relatively small volume chamber and which is discharged into the borehole when the tool is closed. An example of such a device can be found in U.S. Pat. No. 4,416,152. Before closing, a sample can be allowed to flow into a sample tank through a separate but parallel circuit. Other methods provide for the sample to be collected through the same fluid circuit.

When exposed to an open hole, the fluid characteristics of formation fluid can change rapidly, thus it is important that the formation fluid be removed as quickly as possible. However, it is important that the formation flow rate be regulated in order to prevent dropping the fluid pressure below its "bubble-point" since measuring separated fluids does not result in a representative sample. After having these components come out of solution, they typically cannot be easily recombined which results in an unrepresentative sample having altered fluid properties.

Recently developed reservoir testing devices illustrate one method of measuring the bubble-point pressures of the connate fluid at the time of sample collection. This can be accomplished using known techniques of light transmissibility to detect bubbles in the liquid. However this method has some drawbacks when particulate matter is present in the fluid thereby resulting in possible erroneous results. Other methods include trapping a known volume of formation fluid and increasing its volume gradually at a constant temperature. The measured changes in volume and pressure provide a plot of pressure versus volume in order to ascertain the value of the bubble-point. This value is estimated within the region of the plot where the pressure change with volume first deviates from the initial straight line.

Unfortunately the pumping devices currently in use with the above described sampling devices have some inherent drawbacks. For example, control of the electrical or hydraulic actuation means of the presently used pumping systems is not accurate that in turn results in an inability to fully control the speed of the pumps. Not being able to fully control pump speed prohibits the capability of ceasing pumping operations should the pressure of the connate fluid fall below its bubble point and also hinders the ability to accurately measure the bubble point. Since sampling connate fluid at pressures below its bubble point negatively affects the accuracy of the sampling data results. Therefore a need exists for a means of accurately analyzing properties of connate fluid without affecting the condition or state of the fluid.

BRIEF SUMMARY OF THE INVENTION

The present invention includes a method of analyzing acoustic data comprising, inducing an acoustic signal into a fluid, wherein the fluid is in contact with a first and a second reflective interface, recording data representative of acoustic signals over time as they are reflecting from the interfaces, determining a smoothed first derivative with respect to time of the cumulative sum of squares (CSS) of the filtered data, and cross correlating time-shifted versions of the first derivative with itself. Using this method, the time difference associated with the maximum cross correlation may be found, which is the approximate acoustic travel time.

Optionally, the method may further include performing digital frequency filtering of the raw signal and squaring the filtered amplitude signal; this can create a curve proportional to the acoustic energy at each recorded time. The method may further comprise squaring the raw data, taking the cumulative sum of squares (CSS) of the raw amplitude data, and taking a smoothed second or third derivative of the CSS. A local maximum may be obtained by the second derivative.

Occasionally, the maximum cross correlation value is only slightly larger than the next largest cross correlation value and the correct pulse to use is the one associated with the second largest cross correlation value. This can happen when there is a neighboring acoustic pulse, which has approximately the same peak height as the correct pulse but a different pulse width. Therefore, a further step of thresholding may be used to select the correct pulse for the initial estimate of arrival time. This thresholding may include comparing the value of a

DETAILED DESCRIPTION OF THE INVENTION

Figure 1:
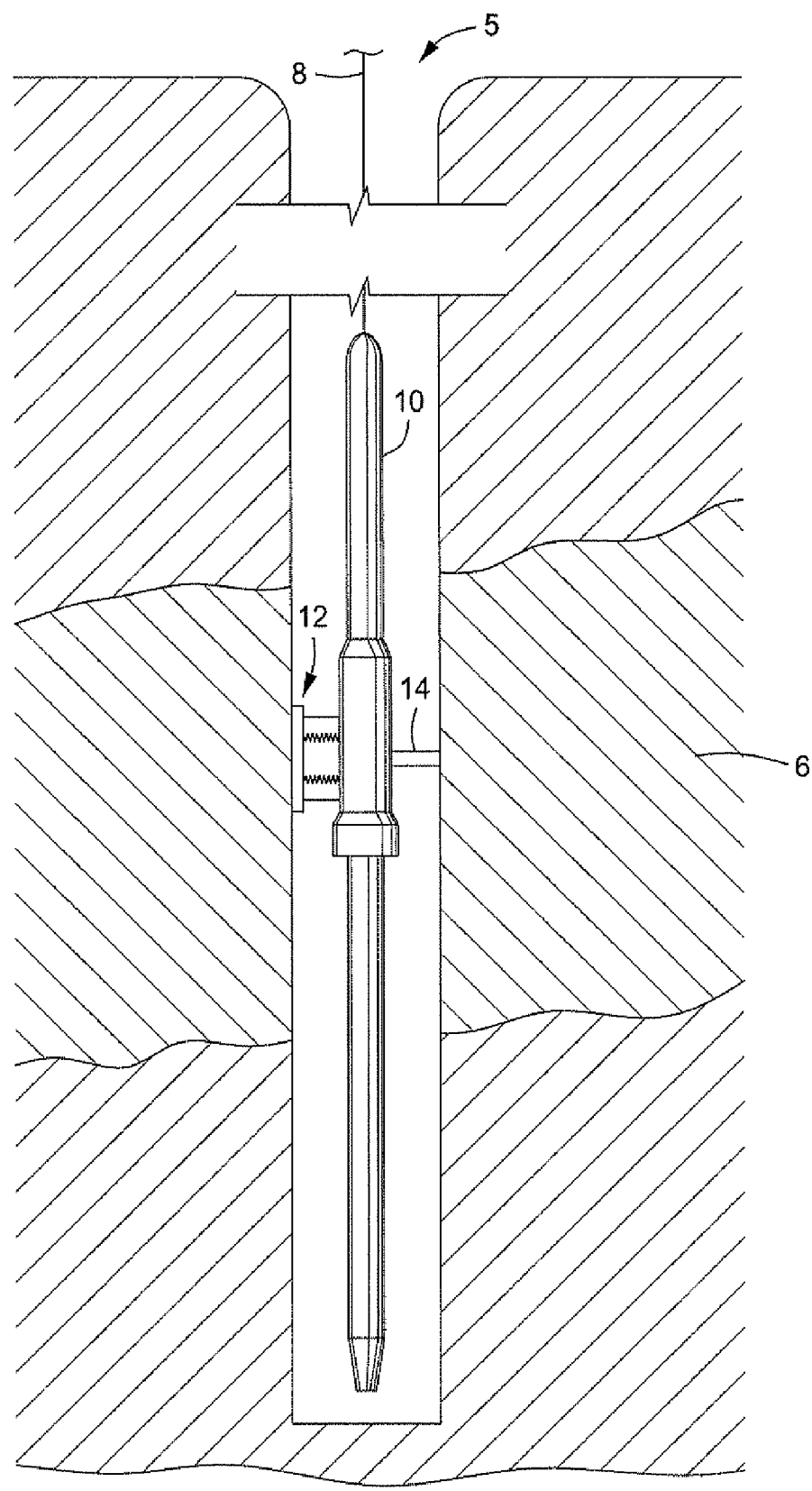
FIG. 1 portrays a sampling sonde disposed in a cut-away of a wellbore.
Figure 2:
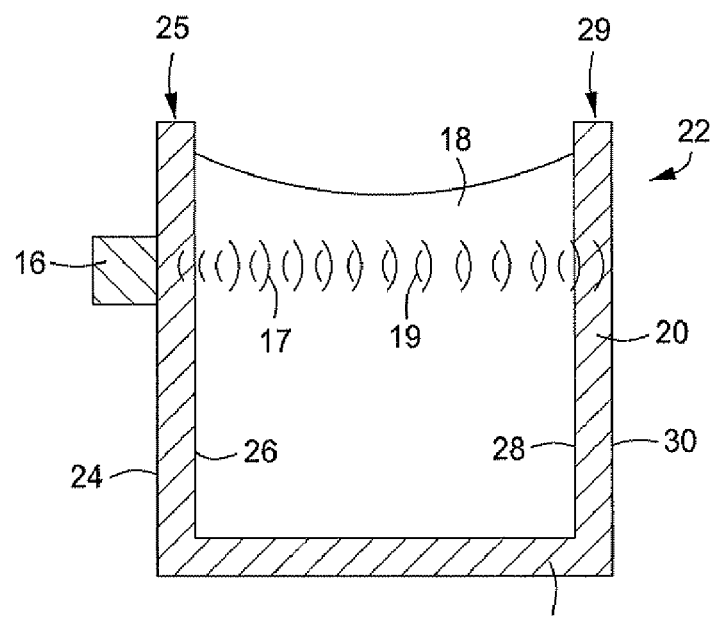
FIG. 2 illustrates a cut-away view of a sampling system.

The method disclosed herein provides a method of acoustically evaluating a fluid sample. The evaluation results comprise fluid sound speed, fluid density, fluid thermal conductivity, and from the change in sound speed with pressure near reservoir pressure, the fluid's equation of state as described in U.S. patent application Ser. No. 11/393,770 filed Mar. 30, 2006. With reference now to FIG. 2, an embodiment of a sampling system 22 of the present device is illustrated in a partial cut-away view. The sampling system 22 of FIG. 2 comprises a vessel 20 in cooperation with a signal generator 16. The outer surface of the container 20 may be radially or rectangularly shaped tubular shaped and may have some outer surfaces that are planar combined with other portions that are curvilinear. Optionally the vessel 20 can be comprised of a conduit or pipe. The vessel 20 can be any container suitable for containing sampled fluid therein.

As shown, the container 20 should be capable of retaining and storing the fluid 18 within its confines during analysis. Although shown as open at its top, the container 20 can also be sealed thereby fully encapsulating the fluid 18 therein. The signal generator 16 can be attached to the outer or first wall 24 of the container 20 or maintained in place. As will be described herein below, for the purposes of reference, both the first and second surfaces (24, 26) shown adjacent to the signal generator 16 are shown as well as the third and fourth surfaces (28, 30) distal from the signal generator 16.

With respect to the signal generator 16, it can be comprised of any device capable of producing an acoustic signal passable through the fluid. This includes traditional acoustic devices such as piezoelectric devices, however other acoustic transducers can also be used to accomplish this function. For example, an Electro-Magnetic Acoustic Transducer (EMAT) can insert ultrasonic waves into metal by electromagnetic coupling. Alternatively, a pulsed laser that strikes an object can generate acoustic waves at a frequency that depends on the laser pulse frequency. Moreover, the signal generator 16 can also be used as a receiver for receiving and recording reflections of the signals generated by the signal generator 16. A flexural mechanical resonator may be coupled for use with the device disclosed herein, an example of a flexural mechanical resonator is described in detail in U.S. Pat. No. 6,938,470 issued Sep. 6, 2005 ('470 patent), the disclosure of which is incorporated for reference herein in its entirety.

Figure 5:
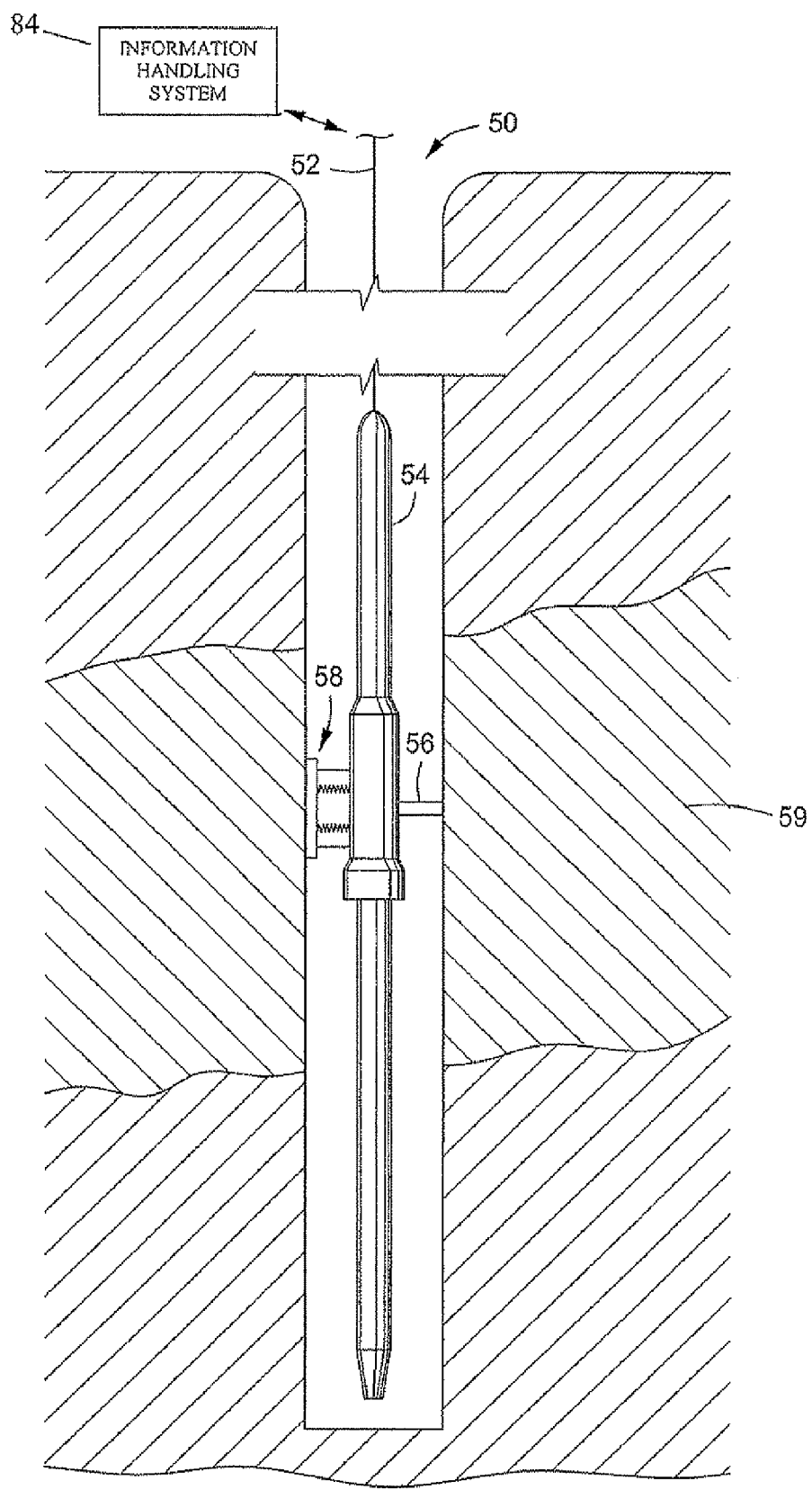
FIG. 5 illustrates a downhole tool configured for use with an embodiment of the method herein described.

In one alternative of the present device, the sampling system 22 is used with the downhole tool 54 of FIG. 5. In the embodiment shown, the downhole tool 54 is equipped with a probe 56 for piercing the wall of the wellbore 50 in order to obtain a sample of connate fluid from the formation 59. The sampling system 22 may be housed within the downhole tool 54 and in fluid communication with the probe 56. Since the probe 56 is in fluid communication with the sampling system 22, fluid sampled by the probe 56 may be delivered to the sampling system 22 via the communication route as soon as it is sampled from the formation 59. Optionally, the sampling system 22 may be disposed outside of the tool 54, such as at the surface, and the sampled fluid can be delivered to the sampling system 22 at some time after it is obtained from the formation 59. Combining the sampling system 22 with the downhole tool 54 provides the advantage of "real time" sampling and reduces the risk of allowing changes in either the pressure or the temperature of the fluid that could in turn affect the sampling results. However, use of the sampling system 22 is not limited to the fluid collection apparatus of FIG. 5, but can be used with any type of device or circuit used in collecting downhole connate fluid.

In one non-limiting example of operation of the present method disclosed herein, after the sampled fluid is delivered to the sampling system 22, the signal generator 16 might be activated for generation of a signal 17 that is emitted into the sampled fluid. Examples of a signal 17 include one or more acoustic pulses. For the purposes of convenience the generated signal 17 is illustrated as a series of curved lines emanating from the transducer 16. After leaving the signal generator 16, the signal 17 passes through the first and second surfaces (24, 26) of the container 20, into the contained fluid 18, and onto the distal third and fourth surfaces (28, 30). A portion of the generated signal 17 (the reflected signal 19) reflects back to the direction of the signal generator 16. Similarly, the reflected signal 19 is illustrated for convenience as a series of curved lines directed towards the signal generator 16. In the embodiment of FIG. 2, the signal generator 16 can operate as a transmitter and also as a signal receiver. Optionally a separate transducer (not shown) could be included that operates solely as a signal receiver for receiving the reflected signals 19. In the embodiment of FIG. 2, the second surface 26 and the third surface 28 act as interfaces from which signals are reflected.

When the signal generator comprises a piezoelectric transducer, a short voltage spike can be applied to the transducer that typically lasts about 1-2 microseconds. This spike causes the transducer to resonate at its resonant frequency, which is typically from about 5 MHz to about 10 MHz. Analogous to a bell that rings for a while after it has been struck by a hammer, the transducer rings, primarily at its resonant frequency, for about a microsecond. An ever-decreasing portion of this microsecond-long pulse bounces back and forth between the tube wall that is bounded by surface 24 and surface 26, (which is in contact with the transducer 16) because a portion of the pulse is transmitted into the fluid 18 upon each bounce off of the surface 26. The transmitted portion of the pulse passes beyond surface 26, enters the fluid 18, reflects from the surface 28, and eventually returns to be detected by the transducer 16. The acoustic transducer serves both as source and receiver. A high-speed (40-70 MHz) analog-to-digital converter may be used for monitoring the signal received by the transducer.

As shown, the signal generator 16 receives and records the reflected signal for subsequent analysis. The recorded signal can either be immediately processed to determine fluid data, transmitted from the downhole tool 54 to a separate site for storage or data processing, or can be recorded within the downhole tool 54 for later analysis.

As is known, the sound speed, c, of a fluid is determined by dividing the travel time of the signal through the fluid 18 by the distance the signal traveled through the fluid. This can be accomplished by designating the letter "d" as the distance between surface 26 and 28. Moreover, the variable 2t can be designated as the time difference between the arrival time of the first echo (corresponding to one round trip going from surface 24 to 26 and back again to 24) and the arrival time of the echo off surface 28 (corresponding to one round trip from 24, past 26, to 28, and eventually, back to 24). Therefore, 2t is amount of time that transpired for sound to travel a round-trip distance (2d) within the fluid 18 from surface 26 to surface 28 and back to surface 26. The sound speed therefore is 2d/2t.

Fluid density can be determined acoustically from the following relationship for an acoustic pulse bouncing back and forth between surface 24 and surface 26:

$$\rho_F = \rho_W(c_W/c_F)[1+\text{Sqrt}(R_{WF})]/[(1-\text{Sqrt}(R_{WF})]; \quad (1)$$

where:
$\rho_W$=Transducer wall density in g/cc,
$\rho_T$=Transducer density in g/cc
$c_W$=Tube wall longitudinal sound speed,
$c_T$=Transducer longitudinal sound speed
$\rho_F$=Fluid density in g/cc,
$c_F$=Fluid sound speed,
$R_{WF}$=Fraction of energy reflected at all/Fluid interface, and
$R_{WF}=(\rho_W c_W - \rho_F c_F)^2/(\rho_W c_W + \rho_F c_F)^2$.

The details of acoustically determining fluid density can be found in pending U.S. Pat. No. 7,024,917 issued Apr. 11, 2006 ('917 patent), the entirety of which is incorporated for reference herein. Fluid density could also be measured by using flexural mechanical resonators as described in the '470 patent. Fluid density could also be determined by any other means such as by measuring the pore pressure gradient across the zone from which the fluid is being extracted. Knowing the fluid's density and measuring its sound speed allows determination of the fluid's compressibility, which is much simpler than the current method of determining compressibility downhole by trapping a volume of fluid, expanding the volume, and measuring the drop in pressure per volume increase.

The bulk modulus B of a fluid is equal to the reciprocal of the compressibility of the fluid, B=1/K. It is also known that the sound speed is equal to the square root of the fluid's bulk modulus divided by the fluid density, $c=(B/\rho)^{1/2}$. Substituting the reciprocal of compressibility for the bulk modulus and isolating compressibility yields the following equation:

$$K=1/(c^2\rho) \quad (2)$$

Accordingly, having determined the fluid density, $\rho$, and the fluid sound speed, c, as described herein, the fluid compressibility can then be calculated using equation (2).

In one embodiment of the method and apparatus herein disclosed, the raw amplitude data can be digitally frequency filtered. One example of digitally frequency filtered comprises applying a digital bandpass filter to reject any frequencies that are not close to the acoustic source frequency. For example, for a 10 MHz acoustic source and a 40 MHz sampling frequency, the raw data could be processed through a 9-11 MHz digital bandpass filter. Next, the square of the amplitude at each sampling time can be computed. This squared value corresponds to the energy received at that time.

A cumulative sum of squared values (CSS) may then be generated. The CSS represents the cumulative sum of energy received up until that time. The digital bandpass filtering and cumulative sum of squares have already smoothed the raw data and removed some noise. However further data smoothing may still be undertaken of the already filtered cumulative sum of squares data. The further smoothing may comprise taking the first and second numerical derivatives of the CSS.

One derivative method includes using the Savitzky-Golay method (Savitzky and Golay, Analytical Chemistry, Vol. 36, No. 8, July 1964), which is based on fitting a polynomial to the curve and computing the derivatives of this polynomial.

Taking the cumulative sum of squares is equivalent to integration and noise averaging (smoothing); a plot of energy pulses is recovered by differentiating this integral. A benefit of integrating followed by differentiation is retention of the smoothing effects of integration and of smoothed numerical differentiation (such as that obtained by using a fitting polynomial in Savitzky-Golay techniques). That is, the smoothed first derivative of the CSS produces a series of smooth peaks representing pulses (packets) of acoustic energy (such as the following peaks of FIG. 4—35, 36, 37, 39, 40, 41 or 65, 67, 69, etc.). Once the approximate travel time has been determined, focus is given to an energy pulse (such as 39 or 72), which occurs later than the initial energy pulse reflection (such as 35 or 65) by the estimated amount of travel time, an improved measurement of travel time can be determined by using the time difference between pinnacles of these peaks (such as pinnacles of peaks 35 versus 39 or of 65 versus 72) instead of simply using the time difference estimated obtained from the cross correlation maximum.

Figure 3:
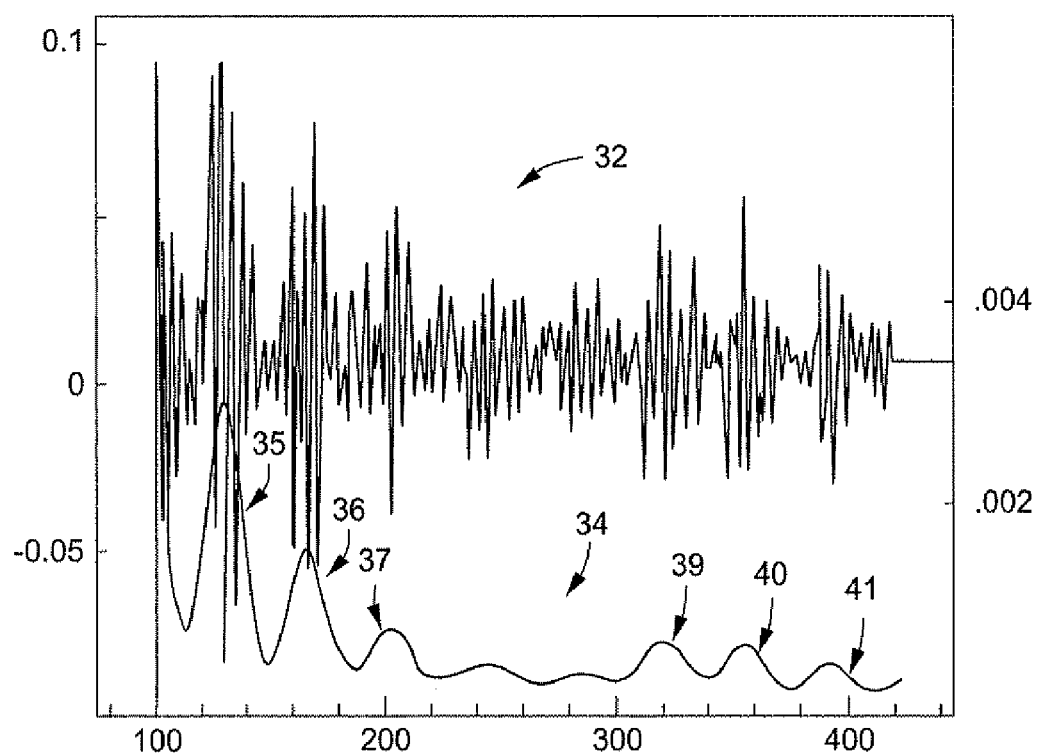
FIG. 3 represents plots containing raw data and processed data.

With reference now to FIG. 3, there is illustrated a plot where the above described smoothing techniques are applied to raw recorded acoustic data. The plot comprises a raw amplitude data plot 32 and a corresponding smooth energy data plot 34. The raw data represents acoustic data received by the transducer 16 in the test set up of FIG. 2. The portion of the raw data that corresponds to the ringing of the transducer immediately after it receives a high voltage spike has been redacted (as well as its corresponding smoothed and threshold data). This plot shows sampling of the signal amplitude at discrete intervals (digital data). To avoid aliasing, the sampling rate is several times the acoustic source frequency. After recording the data, the square of the amplitude for each channel is computed. The amplitude for each channel is proportional to the acoustic intensity (energy) that was received at that channel's time. Next, the cumulative sum (the "integral") of these squared amplitudes is calculated.

As noted above, the data smoothing is further accomplished by computing the first derivative with respect to time of the cumulative sum of squares; and optionally, the Savitzky-Golay method may be implemented for taking a smoothed numerical derivative. Greater high frequency attenuation may be accomplished by using Savitzky-Golay coefficients of lower order (such as square or cube) polynomials over a fairly large number of points (25 channels). The first derivative of the cumulative sum of squares is the smoothed energy received versus time, which shows distinct acoustic energy pulses. The resulting values produced by the Savitzky-Golay method are shown plotted in the smooth energy data plot 34 of FIG. 3.

Figure 4:
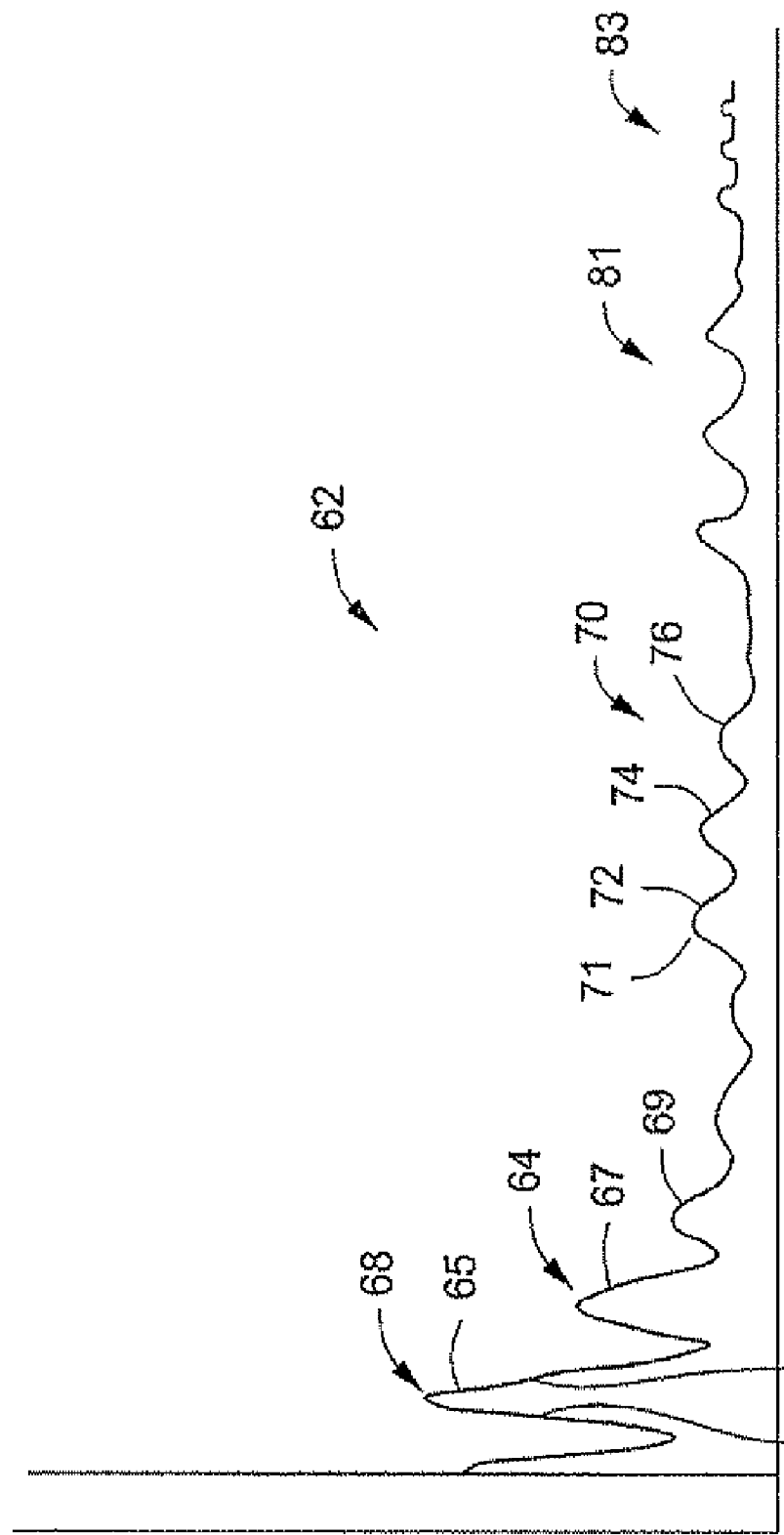
FIG. 4 provides a plot having processed data.

FIG. 4 includes the smoothed data of FIG. 3 that further includes data recorded over a time period greater than that of FIG. 3. As previously discussed with reference to FIG. 2, the acoustic signal produced by the transducer 16 produces reverberations that reflect from the second surface 26 and also from the third surface 28. The peaks of the smoothed data of FIGS. 3 and 4 represent these reverberations. The first series of peaks 64 represent reverberations from the second surface 26 wherein the second series of peaks 70 represent reverberations from the third surface 28. The time difference between the pinnacle (or local maximum 68) of the first peak 65 of the first series and the pinnacle (local maximum 71) of the first peak 72 of the second series 70 represents the acoustic signal travel time from the second surface 26 to the third surface 28 and back. As noted above, this travel time is used in calculating the sound speed of the fluid.

The presence of signals not generated by the transducer 16 can result in a signal peak, such as the noise peaks (81, 83), being mistakenly chosen as the return signal. Thus a method can be employed to ensure proper identification of the return signals. A method of cross correlation can be used to properly identify the set of peaks 72 representing the reverberations from the third surface 28. One example of cross correlation comprises a mathematical algorithm that slides the first set of peaks along the abscissa proximate to the region where the second set of peaks is expected. The respective ordinate values of the signals are then multiplied at that point; the first peak values are then moved along the abscissa some finite amount to an adjacent point, and multiplied again. The first peaks are moved along at these finite amounts over a set interval and the point where the ordinate values are at a maximum identifies the value of the second set of peaks. Thus in an embodiment herein described, cross correlation is performed on the smoothed first derivative data.

The cross correlation process may include an additional optional step of thresholding, wherein the amplitude values of adjacent peaks are compared to ensure a chosen peak is the first peak of a signal series, which usually consists of a triplet of reverberations (such as 35, 36, and 37 or 39, 40, and 41). In this process the amplitude (or ordinate value) of a peak is compared to the next amplitude of the next adjacent peak in the direction towards the origin (i.e. to the left of the peak under consideration). If the ordinate value of the left peak exceeds 70% of the peak under consideration, the left peak is then chosen as the first signal peak and the process is continued. The process is terminated when the ordinate value of the left peak is less than 70% of the peak under consideration.

To obtain a more accurate travel time, the pinnacle of each pulse can be used as the arrival time of that pulse. At the pinnacle, the slope of the energy pulse (the second derivative of the CSS) becomes zero. The acoustic signal over time is collected at evenly spaced time steps. To improve sound speed resolution, interpolation between time steps is performed. Focus is then given to the pair of neighboring time steps (located on either side of a peak's pinnacle such as time steps 78 and 79) for which the second derivative of the CSS has opposite signs. The time at which the second derivative crosses zero is estimated by interpolating between these time steps (78, 79). The sign of the third derivative of the CSS is one way to determine whether a point at which the second derivative of CSS becomes zero represents the pinnacle of a peak (a downward negative curvature) or the lowest point of a valley (an upward positive curvature). Interpolation improves the sound speed resolution by approximately a factor of ten compared to simply rounding to the nearest time step.

In order to determine the local maxima and minima of the first derivative, the second derivative is taken of the cumulative sum of squares using Savitzky-Golay coefficients of a low order and a large number of points. A local maxima (pulse energy peak) from the first derivative curve can be used to obtain a more precise value of the time at which a particular pulse reflection is received by the transducer 16. It should be pointed out that the second derivative crosses zero when the first derivative reaches either its local maxima or local minima. A pulse peak occurs between two channels (78, 79) whenever the second derivative changes from positive (in the left channel 78) to negative (in the right channel 79) with increasing time. Sub-channel time resolution can be achieved by interpolating so as to estimate the location between two channels where the second derivative crosses zero. Alternatively, energy maxima can be distinguished from energy minima (both of which correspond to zeros of the second derivative of the CSS) based on the sign of the third derivative of the CSS.

Using the data obtained from the processed signal, the sound speed of the fluid within the vessel 20 is twice the wall thickness divided by the (round-trip) time between reverberation pulse peaks within the tube wall. The wall sound speed may change with temperature or with pressure of the fluid inside the tube thus causing the wall's acoustic impedance to change. The wall's acoustic impedance must be known to compute fluid density from fluid sound speed and the decay rate of within-wall pulse echo reverberations. Direct downhole measurement of the wall's sound speed can be made from the wall thickness and the time between within-wall pulse peak reverberations. The wall speed is one parameter used to calculate the density of whatever fluid is in contact with the wall. Another factor in calculating fluid density is the wall density but changes in the wall's density with temperature and pressure are a much smaller effect that can usually be ignored or estimated from a table.

The smooth data plot 34 comprises reflected signals both from signal reverberations within the near wall 25 (between the first and second surfaces 24 and 26) as well as a reflection from the far wall 29 (third surface 28). The near wall reflected signals are illustrated as curves (35, 36, 37) on the smooth data plot 34. The far wall reflected signals are also illustrated as curves (39, 40, 41) on the smooth data plot 34. The acoustic signal reverberating within the near wall decays over time, this can be seen in the decreasing local maxima of the curves (35, 36, 37) of the smooth data plot 34 of FIG. 3. Similarly, the amplitude of the signal reflected from the far wall 29 (third surface 28) also decays as illustrated by the decreasing amplitude of the curves (39, 40, 41) representing the far wall 29 reflection.

The downhole tool 54 may be part of a downhole measurement system, wherein the system samples downhole fluid, conducts acoustic tests on the fluid to obtain raw data, and processes the data. The data processing can include the smoothing and the taking of derivatives described above. The measurement system can also include an analyzer that is configured to carry out all or a portion of the above described data processing steps. The analyzer may comprise an information handling system 84. Where the information handling system 84 can be included within the downhole tool 54 or at the surface. When at the surface the information handling system 84 can, as represented by the double-headed arrow, be in constant communication with the downhole tool 54 to receive data, or can be later connected for subsequent data communication. The information handling system 84 may include a processor, memory accessible by the processor, nonvolatile storage area accessible by the processor, and logics for performing each of the steps above described.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, production of the generated signal 17 is not limited to a signal generator 16 disposed within or adjacent to the sampling system 22, but could include signal generators from remote sources. The remote signal sources could be from ballistics, geophones, airguns, or any other known signal-generating source. Additionally, the raw data smoothed and processed in accordance with the methods herein described is not limited to the sampling system of FIG.

2, but can be any type of raw data representing a recorded signal. These and other similar modifications will readily suggest themselves to those skilled in the art, and are intended to be encompassed within the spirit of the present invention disclosed herein and the scope of the appended claims.

What is claimed is:

1. A method of analyzing an acoustic signal propagating in a fluid comprising:
   a) directing an acoustic signal through fluid bounded by a reflective interface so that the acoustic signal reflects from the reflective interface;
   b) recording the acoustic signal;
   c) smoothing the acoustic signal by obtaining a first derivative of the cumulative sum of squares of the amplitude signal;
   d) cross correlating the smoothed first derivative data;
   e) identifying a local maximum in the first derivative data by locating where first derivative data slope is zero;
   f) setting signal arrival time at step (b) to be at the identified local maximum of step (e); and
   g) estimating fluid sound speed based on signal arrival time.

2. The method of claim 1 further comprising taking the second derivative of the smoothed data to identify the local maximum.

3. The method of claim 1, further comprising providing a downhole measurement system within a wellbore that intersects a formation, drawing connate fluid from the formation, directing the fluid into a container having walls to provide the fluid bounded by a reflective interface, and generating the acoustic signal to be directed through the fluid.

4. The method of claim 1 wherein the step of cross correlating comprises thresholding.

5. The method of claim 4 wherein the smoothed data includes a first and second local maximum and the step of thresholding comprises comparing a first local maximum to a second local maximum.

6. The method of claim 5 further comprising determining if the value of the second local maximum is at least 70% of the first local maximum.

7. The method of claim 1, wherein steps (a)-(g) occur in a wellbore.

8. The method of claim 1, wherein steps (a) and (b) occur in a wellbore and steps (c)-(g) occur on surface, the method further comprising transmitting the recorded acoustic signal of step (b) uphole.

9. The method of claim 1, further comprising providing a second reflective interface, measuring the travel time of the acoustic signal between the two interfaces to obtain the sound speed of the connate fluid.

10. A method of analyzing acoustic data comprising:
    inducing an acoustic signal into a fluid, wherein the fluid is in contact with a first and a second reflective interface;
    (a) recording data representative of acoustic signals reflecting from the interfaces;
    (b) applying a smoothing first derivative to the data;
    (c) squaring the raw data;
    (d) obtaining the cumulative sum of squares of the squared data;
    (e) taking the second derivative of the smoothed data and obtaining a value for a local maximum based on the second derivative; and
    (f) cross correlating the smoothed data.

11. The method of claim 10, wherein steps (b)-(f) are performed using an information handling system disposed in a location selected from the list consisting of in a wellbore and on surface.

12. The method of claim 10 further comprising thresholding to identify the reflection from the second interface.

13. The method of claim 12, wherein the smoothed data includes a first and second local maximum and the step of thresholding comprises comparing the value of a first local maximum with the value of a second local maximum.

14. The method of claim 13, further comprising identifying the first local maximum as the second interface reflection based on the ratio of the first local maximum and the second local maximum.

15. The method of claim 10 wherein the fluid is connate fluid obtained from within a subterranean formation and the travel time between the first and second reflective interface represents the fluid sound speed.

16. A downhole measurement system comprising:
    a transmitter;
    a receiver;
    and an analyzer, wherein the analyzer is configured to receive raw acoustic data, conduct first derivative smoothing on the raw data, cross correlate the smoothed data, apply a smoothing first derivative to the data, square the raw data; obtain the cumulative sum of squares of the squared data, and take the second derivative of the smoothed data to obtain a value for a local maximum based on the second derivative.

17. The system of claim 16, further comprising an information handling system.

18. The system of claim 16 wherein the receiver and the transmitter are in the same transducer.

19. The system of claim 16 further comprising a vessel containing fluid.

20. The system of claim 19, wherein the vessel comprises two reflective interfaces.

21. The system of claim 19, wherein the transmitter and receiver are part of a single transducer.

22. The system of claim 21, wherein the transducer is disposed on the vessel.

23. The system of claim 16 further comprising a connate fluid sampling probe configured to draw connate fluid from a subterranean formation.

* * * * *